US012642898B2

(12) United States Patent
White et al.

(10) Patent No.: US 12,642,898 B2
(45) Date of Patent: Jun. 2, 2026

(54) MEDICAL FLUID GENERATION SYSTEM

(71) Applicants:BAXTER HEALTHCARE SA, Glattpark (CH); BAXTER INTERNATIONAL INC., Deerfield, IL (US)

(72) Inventors: James White, Grayslake, IL (US); Jonas Fors, Malmö (SE); Fréderic Vandemaele, Lubbeek (BE); Stefano Ganzerli, Medolla (IT); Olof Jansson, Vellinge (SE); Thomas Hertz, Lund (SE); Michael Pettersson, Malmö (SE); Per-Olof Borgqvist, Lund (SE); Sven Gustafson, Lund (SE); Roland Persson, Limhamn (SE); Jonas Alson, Lund (SE); Anna Szilagyi, Lund (SE)

(73) Assignees: VANTIVE HEALTH GMBH, Glattpark (CH); VANTIVE US HEALTHCARE LLC, Deerfield, IL (US)

( * ) Notice: Subject to any disclaimer, the term of this patent is extended or adjusted under 35 U.S.C. 154(b) by 452 days.

(21) Appl. No.: 18/032,761

(22) PCT Filed: Oct. 21, 2021

(86) PCT No.: PCT/EP2021/079152
§ 371 (c)(1),
(2) Date: Apr. 19, 2023

(87) PCT Pub. No.: WO2022/084425
PCT Pub. Date: Apr. 28, 2022

(65) Prior Publication Data
US 2023/0405196 A1      Dec. 21, 2023

(30) Foreign Application Priority Data
Oct. 22, 2020      (IT) ........................ 102020000025108

(51) Int. Cl.
*A61M 39/10*      (2006.01)
*A61M 1/16*      (2006.01)
*A61M 1/28*      (2006.01)

(52) U.S. Cl.
CPC ........ *A61M 1/1656* (2013.01); *A61M 1/1668* (2014.02); *A61M 1/168* (2013.01);
(Continued)

(58) Field of Classification Search
CPC .. A61M 1/1656; A61M 1/1668; A61M 1/168; A61M 1/287; A61M 39/10; A61M 2209/045
See application file for complete search history.

(56) References Cited

U.S. PATENT DOCUMENTS 4,326,526 A      4/1982      Buck et al.
6,663,829 B1      12/2003      Kjellstrand
(Continued)

FOREIGN PATENT DOCUMENTS

EP      0790051 A2      8/1997

OTHER PUBLICATIONS

International Search Report from International Patent Application No. PCT/EP2021/079152, mailed Jan. 26, 2022, 6 pages.
(Continued)

*Primary Examiner* — John Kim
(74) *Attorney, Agent, or Firm* — K&L Gates LLP

(57) ABSTRACT

A peritoneal dialysis fluid generation system including water purification equipment configured to provide purified water; a presterilized tubing set including a container for storing peritoneal dialysis fluid; at least one glucose or buffer concentrate; and a hemodialysis machine in fluid communication with the water purification equipment. The hemodialysis machine includes at least one mixing pump for mixing the at least one glucose or buffer concentrate with the
(Continued)

purified water to form peritoneal dialysis fluid, a dialysis fluid pump for delivering the peritoneal dialysis fluid to the container, and a control unit configured to control the at least one mixing pump to form the peritoneal dialysis fluid and the dialysis fluid pump to deliver the peritoneal dialysis fluid to the container.

8 Claims, 5 Drawing Sheets

(52) U.S. Cl.
CPC ............ *A61M 1/287* (2013.01); *A61M 39/10* (2013.01); *A61M 2209/045* (2013.01)

(56) References Cited

U.S. PATENT DOCUMENTS

| | | | |
|---|---|---|---|
| 7,108,790 | B2 | 9/2006 | Collins et al. |
| 2007/0265594 | A1 | 11/2007 | Hagermark et al. |
| 2015/0283322 | A1 | 10/2015 | Hachey et al. |
| 2019/0021947 | A1 | 1/2019 | Bomgaars et al. |
| 2019/0321536 | A1 | 10/2019 | Manda et al. |
| 2020/0122087 | A1 | 4/2020 | Jansson et al. |
| 2020/0197589 | A1 | 6/2020 | Peesapati et al. |

OTHER PUBLICATIONS

Written Opinion from International Patent Application No. PCT/EP2021/079152, mailed Jan. 26, 2022, 14 pages.

MEDICAL FLUID GENERATION SYSTEM

PRIORITY CLAIM

This application is a national phase entry of PCT/EP2021/ 079152, filed Oct. 21, 2021, which claims priority to Italian Patent Application No. 102020000025108, filed Oct. 22, 2020, the entire disclosures of which are incorporated herein by reference.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion. HD fluids are typically created by the dialysis machines by mixing concentrates and clean water.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is delivered directly to the extracorporeal circuit, providing convective clearance. Here, more fluid than the patient's excess fluid is removed from the patient, causing the increased convective transport of waste products from the patient. The additional fluid removed is replaced via the substitution or replacement fluid.

Another type of kidney failure therapy is peritoneal dialysis ("PD"), which infuses a dialysis solution, also called dialysis fluid, into a patient's peritoneal cavity via a catheter. The dialysis fluid is in contact with the peritoneal membrane in the patient's peritoneal cavity. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times. PD fluids are typically prepared in a factory and shipped to the patient's home in ready-to-use bags.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment, where fluid transport is driven by gravity. If initially full of used dialysis fluid, the patient manually connects an implanted catheter to a drain to allow the used or spent dialysis fluid to drain from the patient's peritoneal cavity. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day. If the patient is not initially full of used dialysis fluid, the sequence is instead fill, dwell and drain. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the chamber and for the transfer of waste, toxins and excess water to take place. The source may include multiple liters of dialysis fluid including several solution bags.

APD machines pump used or spent dialysate from the peritoneal cavity, through the catheter, and to the drain. As with the manual process, several drain, fill and dwell cycles occur during dialysis. A "last fill" may occur at the end of the APD treatment. The last fill fluid may remain in the peritoneal cavity of the patient until the start of the next treatment, or may be manually emptied at some point during the day.

A large percentage of blood treatments, such as HD, HF and HDF treatments, take place in a clinic or center. The blood machines in the clinics or centers are typically used throughout the day. Nevertheless, there exists a fairly significant period of time after the clinic or center closes, where the machines are not used. A certain amount of time is needed for the machines to run a thorough disinfection sequence prior to the next day's treatments, but even still, a substantial amount of time remains during which the blood machines are dormant and unused.

It is known from document US2019021947 a sterile solution product bag including sterilization grade filter integrated directly into the product bag such that microbial and particulate matter filtration can be performed using the filter directly at the point of fill. The filter can include a hollow fiber filter membrane contained in a stem connected to a bladder of the product bag.

It is further known from document U.S. Pat. No. 7,108, 790 an apparatus for generating sterile infusion fluid from non-sterile infusion fluid produced by a machine. The sterile infusion fluid is produced by a sterile fluid generating device used in conjunction with a dialysis machine resulting in sterile infusion fluid being produced.

A need exists accordingly to provide an improved system to maximize the dialysis fluid producing potential of in-center dialysis machines, such as hemodialysis machines, which allows patients to be treated at home instead of having to travel back and forth to a clinic, and which allows in-center dialysis machines to help in times of increased demand or urgent need of dialysis fluids such as PD fluids.

SUMMARY

The present disclosure sets forth systems and methods for producing peritoneal dialysis ("PD") fluid and other fluids using one or more in-center hemodialysis ("HD") machine. While the present disclosure focuses mainly on PD fluid, the teachings discussed herein also applicable to other treatment and injectable fluids, such as continuous renal replacement treatment ("CRRT") fluids including HD fluids, substitution or replacement fluids for hemofiltration ("HF") and hemo-diafiltration ("HDF"), saline, lactated ringers and the like. The in-center hemodialysis machine receives purified water from a central water purification station in one embodiment. In a PD fluid example, the purified water is mixed with PD concentrates when making PD fluid, including electrolyte, glucose and buffer concentrates, and is then delivered via a presterilized tubing set to one or more presterilized storage container or bag. One or more terminal or sterile sterilizing grade filters, e.g., integral to the final solution container, is/are provided with the tubing set to sterilize the PD fluid to the point that it may be delivered to a patient's peritoneal cavity (or elsewhere for the other fluids listed above). In one embodiment, the one or more filters is/are provided in the tubing set upstream of multiple containers or bags, which are ganged in series, in parallel or both in the same tubing set. Alternatively or additionally, a sterile sterilizing grade filter is arranged downstream of the container or bag.

A pressure transmission line may be provided in the tubing set, which extends from a point just upstream from the one or more sterile sterilizing grade filters back to a pressure port (normally used for arterial or venous pressure) of the hemodialysis machine, and which allows the PD fluid pressure to be measured while one or more containers are filled. When the pressure along the pressure transmission line changes by a characteristic amount, filling is complete and the hemodialysis machine stops PD fluid production and delivery. Alternatively, any of the systems described herein may use other volumetric controls, such as, counting known stroke volumes of the pump of the dialysis machine that is used to pump the dialysis fluid, using a balance chamber, using a known flowrate and time, using a weigh scale, and/or using a sensor at the container or bag for detecting a filled liquid level, e.g., an optical or capacitance sensor. It is also contemplated that any of the systems described herein may fill multiple containers or bags as part of the disposable set of containers or bags, e.g., in series, parallel or both.

In one embodiment, a return line is provided from the filled containers to the hemodialysis machine. The return line allows for a PD fluid sample to be taken and analyzed in the machine. The machine may, for example, provide an onboard conductivity sensor in the machine's drain line (and optionally a glucose sensor), which may be accessed to evaluate the sample. If needed, one or more sterile sterilizing grade filters may be provided in the return line to prevent contamination of the sample and the PD fluid residing upstream in the container and tubing set.

In another embodiment, a standalone valve station may be provided, which is positioned to operate with the fill lines leading to a plurality of PD fluid containers or bags. The standalone valve station may be a delegate-type unit that takes commands from the hemodialysis machine. The valve station selectively opens and closes the fill lines according to a desired filling pattern, which allows a desired container, or group of containers, to be filled with PD fluid at a certain time and in a certain order. The valve station also allows different chemical formulations of PD (or other treatment) fluids to be produced and delivered to different containers of the tubing set.

In an alternative embodiment, instead of filling the containers or bags with finished PD (or other treatment) fluid, the hemodialysis machines form distinct component solutions that are delivered to separate chambers of a dual chamber container. For PD, the hemodialysis machine in any order mixes glucose concentrate with purified water to produce a glucose solution, which is then delivered to a glucose solution chamber of one or more containers. The hemodialysis machine mixes buffer concentrate with purified water to produce a buffer solution, which is then delivered to a buffer solution chamber of the one or more containers. The glucose and buffer chambers are separated by a frangible seal, for example, which a patient or caregiver opens at the time of use. The component solutions are then mixed to form an overall PD fluid for treatment. Separating the PD fluid into component solutions for storage may increase the overall shelf life of container product. An overpouch may also be provided to cover the multi-chamber containers to protect the component solutions from degradation over time.

CRRT fluids including HD fluids, substitution or replacement fluids for HF and HDF, saline, lactated ringers and the like use different concentrates than PD fluid and therefore yield different concentrate solutions in the dual chamber container. It is also contemplated to provide at least one additional chamber as desired, for a third or further additional component solution, e.g., an additional glucose solution for a final PD fluid. In a further alternative embodiment, any of the chambers, including the additional third chamber may be prefilled with a component solution, which is also presterilized. In a three chamber container example, one chamber may be prefilled, while the other two chambers are filled via the hemodialysis machine.

Any of the systems described herein may operate additionally with a reusable filter, such as an ultrafilter or a dialyzer, which may for example be mounted at the dialysis machine. In an ultrafilter example, the ultrafilter inlet is connected to a reusable hemodialysis machine supply line, while the ultrafilter outlet is connected to the presterilized tubing set of the single chamber or multi-chamber container systems described herein. The tubing sets may not need one or more additional sterile sterilizing grade filter, however, such one or more filter may be provided, for example, to protect against any contamination resulting from the connection of the presterilized tubing set to the ultrafilter or dialyzer. The reusable filters provide additional or alternative sterilization.

Any of the filled PD (or other treatment) fluid containers discussed herein may be separated from a remainder of a tubing or disposable set using a handheld heat sealer, which seals a tube closed directly adjacent to the container. Once sealed (or double sealed for extra safety) the tube may be cut using scissors or the heat sealer itself. The separate filled PD fluid container may then be labeled and transported for packaging and delivery, e.g., to a home PD patient's residence. Labels may be printed at the hemodialysis machine, at a separate dedicated label printer or at a standard printer, e.g., via instructions sent from the hemodialysis machine.

In light of the disclosure set forth herein, and without limiting the disclosure in any way, in a first aspect, which may be combined with any other aspect or portion thereof described herein, a peritoneal dialysis fluid generation system includes water purification equipment configured to provide purified water; a presterilized tubing set including a container for storing peritoneal dialysis fluid; at least one glucose or buffer concentrate; and a hemodialysis machine in fluid communication with the water purification equipment, the hemodialysis machine including at least one mixing pump for mixing the at least one glucose or buffer concentrate with the purified water to form peritoneal dialysis fluid, a dialysis fluid pump for delivering the peritoneal dialysis fluid to the container, and a control unit configured to control the at least one mixing pump to form the peritoneal dialysis fluid and the dialysis fluid pump to deliver the peritoneal dialysis fluid to the container.

In a second aspect, which may be combined with any other aspect or portion thereof described herein, the hemodialysis machine includes at least one of (i) at least one conductivity sensor or (ii) a glucose sensor outputting to the control unit as feedback to form the peritoneal dialysis fluid.

In a third aspect, which may be combined with any other aspect or portion thereof described herein, the water purification equipment includes a central water purification station configured to feed a plurality of hemodialysis machines or a standalone water purifier configured to feed the hemodialysis machine.

In a fourth aspect, which may be combined with any other aspect or portion thereof described herein, the control unit is configured to enable an operator to enter at least one of (i) a volume of peritoneal dialysis fluid per container or (ii) a number of containers to be filled with peritoneal dialysis fluid.

In a fifth aspect, which may be combined with any other aspect or portion thereof described herein, the peritoneal dialysis fluid generation system includes a filter located in the tubing set upstream from the container, the filter configured to further purify the peritoneal dialysis fluid for delivery to a patient's peritoneal cavity.

In a sixth aspect, which may be combined with any other aspect or portion thereof described herein, the control unit is configured to perform a pressure integrity test on the filter.

In a seventh aspect, which may be combined with any other aspect or portion thereof described herein, the peritoneal dialysis fluid generation system includes a pressure transmission line in fluid communication with the container, the pressure transmission line configured to transmit peritoneal dialysis fluid dialysis fluid pressure to a pressure transducer of the hemodialysis machine, the control unit configured to look for a characteristic change in peritoneal dialysis fluid pressure to stop the dialysis fluid pump from delivering the dialysis fluid to the container.

In an eighth aspect, which may be combined with any other aspect or portion thereof described herein, the container is a first container, and which includes a second container placed fluidly in series with the first container.

In a ninth aspect, which may be combined with any other aspect or portion thereof described herein, the container is a first container, and which includes a second container placed fluidly in parallel with the first container.

In a tenth aspect, which may be combined with any other aspect or portion thereof described herein, the container is a first container, and which includes a second container placed fluidly in series with the first container and a third container placed fluidly in parallel with the first container.

In an eleventh aspect, which may be combined with any other aspect or portion thereof described herein, the container is a first container, and which includes a second container for receiving the peritoneal dialysis fluid, the system including a first filling tube leading to the first container and a second filling tube leading to the second container, and which includes first and second clamps on the outside of the hemodialysis machine for selectively opening or occluding the first and second filling tubes.

In a twelfth aspect, which may be combined with any other aspect or portion thereof described herein, the container is a first container, and which includes a second container for receiving the peritoneal dialysis fluid, the system including a first filling tube leading to the first container and a second filling tube leading to the second container, and which further includes a standalone valve station for selectively opening or occluding the first and second filling tubes.

In a thirteenth aspect, which may be combined with any other aspect or portion thereof described herein, the standalone valve station is in wired or wireless communication with the control unit of the hemodialysis machine for commanding the standalone valve station.

In a fourteenth aspect, which may be combined with any other aspect or portion thereof described herein, the system is configured to operate the standalone valve station to deliver the peritoneal dialysis fluid in a first formulation to the first container and to deliver the peritoneal dialysis fluid in a second formulation to the second container.

In a fifteenth aspect, which may be combined with any other aspect or portion thereof described herein, the peritoneal dialysis fluid generation system includes a return line from the container to the hemodialysis machine for testing the peritoneal dialysis fluid, and wherein the testing optionally includes composition or sterility testing.

In a sixteenth aspect, which may be combined with any other aspect or portion thereof described herein, wherein at least one of (i) the purified water is sterilized water or (ii) the system includes a heat sealer for sealing closed a filling line leading to the container.

In a seventeenth aspect, which may be combined with any other aspect or portion thereof described herein, a medical fluid generation system includes water purification equipment configured to provide purified water; a container including a first chamber and a second chamber; a first concentrate; a second concentrate; and a hemodialysis machine in fluid communication with the water purification equipment, the hemodialysis machine including at least one mixing pump for mixing the first and second concentrates with purified water to form a first solution and a second solution, at least one dialysis fluid pump for delivering the first solution and the second solution, and a control unit configured to control the at least one mixing pump to form the first solution and the second solution and the at least one dialysis fluid pump to deliver the first solution to the first chamber of the container and the second solution to the second chamber of the container.

In an eighteenth aspect, which may be combined with any other aspect or portion thereof described herein, the medical fluid generation system is a peritoneal dialysis fluid generation system, and wherein the first concentrate is a buffer concentrate and the second concentrate is a glucose concentrate.

In a nineteenth aspect, which may be combined with any other aspect or portion thereof described herein, wherein the container is a first container and which includes a second container having first and second chambers, and wherein the control unit is configured to deliver the first solution to the first chamber of each of the first and second containers and the second solution to the second chamber of each of the first and second containers.

In a twentieth aspect, which may be combined with any other aspect or portion thereof described herein, the container is provided as part of a tubing set including a first filling line leading to the first chamber of the container and a second filling line leading to a second chamber of the container.

In a twenty-first aspect, which may be combined with any other aspect or portion thereof described herein, the tubing set includes a filter located upstream and/or downstream of the first and second filling lines.

In a twenty-second aspect, which may be combined with any other aspect or portion thereof described herein, the tubing set includes (i) a first manifold line in fluid communication with a plurality of first filling lines leading to the first chambers of a plurality of the containers and (ii) a second manifold line in fluid communication with a plurality of second filling lines leading to the second chambers of the plurality of the containers.

In a twenty-third aspect, which may be combined with any other aspect or portion thereof described herein, the first and second chambers of the container are separated by at least one frangible seal, the frangible seal openable to allow the first solution to mix with the second solution.

In a twenty-fourth aspect, which may be combined with any other aspect or portion thereof described herein, the medical fluid generation system includes a filter located upstream from the container, the filter configured to further purify the first solution and the second solution for delivery to a patient's peritoneal cavity after mixing.

In a twenty-fifth aspect, which may be combined with any other aspect or portion thereof described herein, the container includes a third chamber prefilled with a third solution different than the first and second solutions.

In a twenty-sixth aspect, which may be combined with any other aspect or portion thereof described herein, the container includes a third chamber prefilled with a third solution made from one of the first or second concentrates.

In a twenty-seventh aspect, which may be combined with any other aspect or portion thereof described herein, the container includes a third chamber, and wherein the control unit is further configured to control the at least one mixing pump to form a third solution from a third concentrate and the at least one dialysis fluid pump to deliver the third solution to the third chamber of the container.

In a twenty-eighth aspect, which may be combined with any other aspect or portion thereof described herein, the container includes a third chamber, and wherein the control unit is further configured to control the at least one mixing pump to form a third solution from one of the first or second concentrates and the at least one dialysis fluid pump to deliver the third solution to the third chamber of the container.

In a twenty-ninth aspect, which may be combined with any other aspect or portion thereof described herein, a medical fluid generation system includes water purification equipment configured to provide purified water; a container for storing medical fluid; a pressure transmission line in fluid communication with the container and configured to transmit medical fluid pressure; at least one concentrate for the medical fluid; and a hemodialysis machine in fluid communication with the water purification equipment, the hemodialysis machine including a pressure transducer positioned and arranged to sense the medical fluid pressure in the pressure transmission line, at least one mixing pump for adding the at least one concentrate with the purified water to form the medical fluid, a dialysis fluid pump for delivering the medical fluid to the container, and a control unit configured to (i) control the at least one mixing pump to form the medical fluid, (ii) control the dialysis fluid pump to deliver the medical fluid to the container, and (iii) look for a characteristic change in medical fluid pressure to stop the dialysis fluid pump from delivering the medical fluid to the container.

In a thirtieth aspect, which may be combined with any other aspect or portion thereof described herein, the characteristic change in medical fluid pressure is a characteristic change in static medical fluid pressure.

In a thirty-first aspect, which may be combined with any other aspect or portion thereof described herein, a medical fluid generation system includes water purification equipment configured to provide purified water; a container including a first chamber for storing purified water and at least one second chamber prefilled with a concentrate for the medical fluid; and a hemodialysis machine in fluid communication with the water purification equipment, the hemodialysis machine including a fluid pump for delivering the purified water to the first chamber of the container.

In a thirty-second aspect, which may be combined with any other aspect or portion thereof described herein, the plurality of chambers are separated by at least one frangible seal openable to allow the purified water to mix with the at least one concentrate.

In a thirty-third aspect, which may be combined with any other aspect or portion thereof described herein, the purified water mixed with the concentrate forms peritoneal dialysis fluid.

In a thirty-fourth aspect, which may be combined with any other aspect or portion thereof described herein, a tubing set for use with a machine that generates a medical fluid, wherein the tubing set includes a line for connecting to the machine or to a fluid carrying structure extending from the machine; at least one sterile sterilizing grade filter located along the line; a manifold structure in fluid communication with the line; a plurality of fill lines in fluid communication with the manifold structure; and a plurality of medical fluid containers, each fill line in fluid communication with one of the medical fluid containers, wherein each of the line, the at least one sterile sterilizing grade filter, the manifold structure, the plurality of fill lines and the plurality of medical fluid containers are connected and sterilized prior to use.

In a thirty-fifth aspect, which may be combined with any other aspect or portion thereof described herein, the manifold structure is a manifold connector.

In a thirty-sixth aspect, which may be combined with any other aspect or portion thereof described herein, the tubing set includes patient tubing provided with each of the medical fluid containers.

In a thirty-seventh aspect, which may be combined with any other aspect or portion thereof described herein, the patient tubing is provided in an overpouch.

In a thirty-eighth aspect, which may be combined with any other aspect or portion thereof described herein, the overpouch additionally covers the respective medical fluid container.

In a thirty-ninth aspect, which may be combined with any other aspect or portion thereof described herein, the plurality of medical fluid containers are placed fluidically in parallel via fluid communication with the fill lines and the manifold structure.

In a fortieth aspect, which may be combined with any other aspect or portion thereof described herein, at least one of the plurality of medical fluid containers is placed fluidically in series with an additional medical fluid container.

In a forty-first aspect, which may be combined with any other aspect or portion thereof described herein, at least one of the plurality of medical fluid containers is placed fluidically in series with a first additional medical fluid container and fluidically in parallel with a second additional medical fluid container.

In a forty-second aspect, which may be combined with any other aspect or portion thereof described herein, the tubing set includes a return line extending from at least one of the medical fluid containers for connection to the machine or to a machine line extending from the machine and optionally wherein the return line includes at least one sterile sterilizing filter.

In a forty-third aspect, which may be combined with any other aspect or portion thereof described herein, the fluid carrying structure extending from the machine includes an ultrafilter or dialyzer having an inlet line configured to connect to the machine or a line extending from the machine.

In a forty-fourth aspect, which may be combined with any other aspect or portion thereof described herein, the tubing set is assembled and sterilized originally in a first package and the ultrafilter or dialyzer and inlet line are assembled and sterilized originally in a second package.

In a forty-fifth aspect, which may be combined with any other aspect or portion thereof described herein, a tubing set for use with a machine that generates a medical fluid, wherein the tubing set includes a line for connecting to the machine or to a fluid carrying structure extending from the machine; a Y or T-connector in fluid communication with the line; a first manifold line in fluid communication with the Y or T-connector; a second manifold line in fluid communication with the Y or T-connector; a plurality of multi-chamber medical fluid containers each including a first chamber and a second chamber; a plurality of first filling lines in fluid communication with the first manifold line and the first chambers of the plurality of multi-chamber medical fluid containers; a plurality of second filling lines in fluid communication with the second manifold line and the second chambers of the plurality of multi-chamber medical fluid containers; and at least one sterile sterilizing filter located (i) upstream of the Y or T-connector or (ii) in each of the first and second manifold lines.

In a forty-sixth aspect, which may be combined with any other aspect or portion thereof described herein, the Y or T-connector is a first Y or T-connector, and which includes a second Y or T-connector located (i) between a leg of the first Y or T-connector and one of first or second manifold lines or (ii) upstream of the at least one sterile sterilizing filter when the at least one sterile sterilizing filter is located upstream of the first Y or T-connector, and wherein a disposable drain line extends from a leg of the second Y or T-connector.

In a forty-seventh aspect, which may be combined with any other aspect or portion thereof described herein, at least one of the multi-chamber medical fluid containers includes a third chamber, the third chamber prefilled with a component solution.

In a forty-eighth aspect, which may be combined with any other aspect or portion thereof described herein, at least one of the multi-chamber medical fluid containers includes a third chamber, and which includes a third filling line in fluid communication with the third chamber and in selective fluid communication with the line for connecting to the machine or to a fluid carrying structure extending from the machine.

In a forty-ninth aspect, which may be combined with any other aspect or portion thereof described herein, the fluid carrying structure extending from the machine includes an ultrafilter or dialyzer having an inlet line configured to connect to the machine or a line extending from the machine.

In a fiftieth aspect, which may be combined with any other aspect or portion thereof described herein, the tubing set is assembled and sterilized originally in a first package and the ultrafilter or dialyzer and inlet line are assembled and sterilized originally in a second package.

In a fifty-first aspect, which may be combined with any other aspect or portion thereof described herein, a medical fluid generation method includes purifying water; mixing the purified water to form a medical fluid; filtering the medical fluid using at least one sterile sterilizing filter; and delivering the filtered medical fluid to a plurality of presterilized medical fluid containers in parallel, in series or in parallel and series.

In a fifty-second aspect, which may be combined with any other aspect or portion thereof described herein, a method for preparing a medical fluid is provided comprising: providing a dual compartment syringe, wherein the first compartment includes a first liquid concentrate and the second compartment includes a second liquid concentrate; providing a saline bag; injecting the first liquid concentrate and the second liquid concentrate into the saline bag to form a mixture, the mixture being a suitable peritoneal dialysis fluid or a suitable CRRT solution for feeding renal failure medical devices.

In a fifty-third aspect, which may be combined with any other aspect or portion thereof described herein, the dual compartment syringe comprises a mixing nozzle configured to be connected to the saline bag to allow spiking the solutions with the first and second liquid concentrates, in particular, the dual compartment syringe keeping the first and second liquid concentrates separated during handling and allowing first and second liquid concentrates to mix together when injecting into the saline bag.

In a fifty-fourth aspect, which may be combined with any other aspect or portion thereof described herein, the first liquid concentrate includes glucose, and/or the second liquid concentrate includes a buffer, such as lactate or bicarbonate, the mixture being a peritoneal dialysis fluid. Alternatively, the first liquid concentrate includes electrolytes comprising sodium, magnesium, calcium, and/or the second liquid concentrate includes a buffer, such as lactate or bicarbonate, the mixture being a CRRT solution.

In a fifty-fifth aspect, which may be combined with any other aspect or portion thereof described herein, volumes of the first and second liquid concentrates are in a prefixed volume ratio in the dual compartment syringe and are pre-measured in the syringe based on a volume of the saline bag into which the first and second liquid concentrates are to be injected.

Additionally, any of the above aspects, or portions thereof, and/or any of the features, functionality and alternatives described in connection with any one or more of FIGS. 1A to 4 may be combined with any of the features, functionality and alternatives described in connection with any other of FIGS. 1A to 4.

It is accordingly an advantage of the present disclosure to provide a system that makes fresh dialysis fluid when time is available to do so, e.g., when one or more hemodialysis machine at a hospital or clinic is not being used.

It is another advantage of the present disclosure to provide a system that makes fresh dialysis fluid for a hospital or clinic with minimal resource impact to the hospital or clinic.

It is a further advantage of the present disclosure to provide a system that makes fresh dialysis fluid at or near a hospital or clinic, e.g., near where it will be used, and which is of a high quality.

It is yet a further advantage of the present disclosure to provide a system that makes fresh dialysis fluid at or near a hospital or clinic, and which is placed in a container for later use.

Moreover, it is an advantage to make sterilized fluids, such as PD fluids, CRRT fluids, saline, lactated ringers and the like closer in time and distance to a point of use for the patient, which lessens the amount of supplies that have to be stored, e.g., at a patient's home.

It is still a further advantage to prepare PD fluid using one or more in-center hemodialysis machine.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE DRAWINGS

FIG. 2 is a front view illustrating an alternative system of the present disclosure using an in-center dialysis machine to prepare and store peritoneal dialysis ("PD") fluid component solutions for later mixing to form a PD fluid or other sterilized fluid, such as CRRT fluids including HD fluids and substitution or replacement fluids for HF and HDF, saline, lactated ringers and the like.

DETAILED DESCRIPTION

Figure 1A:
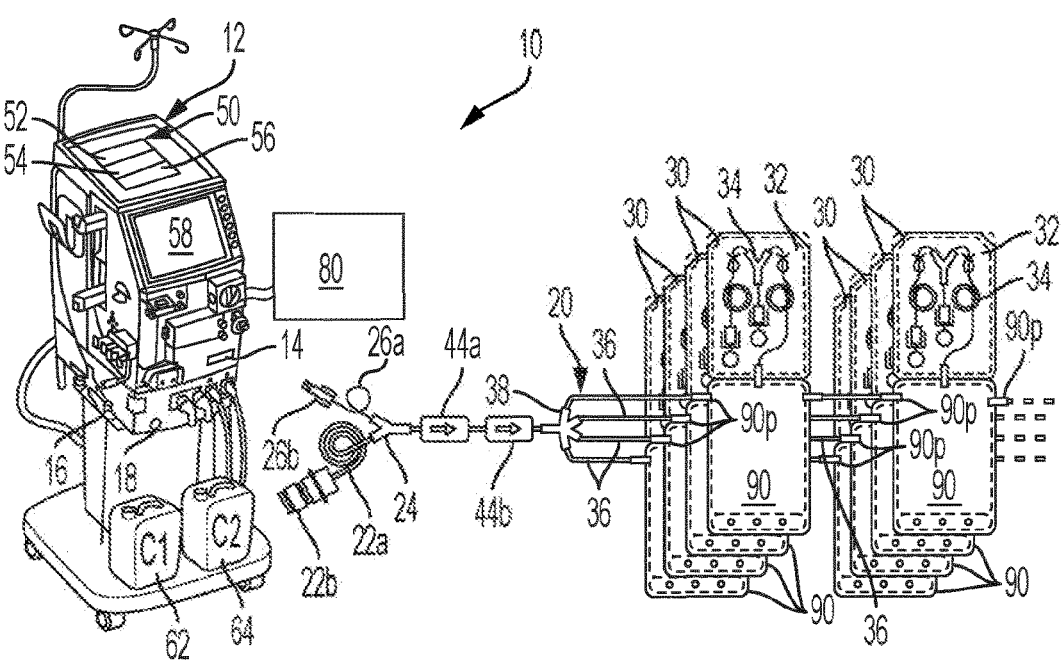
FIGS. 1A to 1C are perspective views illustrating one system of the present disclosure for preparing and storing peritoneal dialysis ("PD") fluid using an in-center dialysis machine.
Figure 1B:
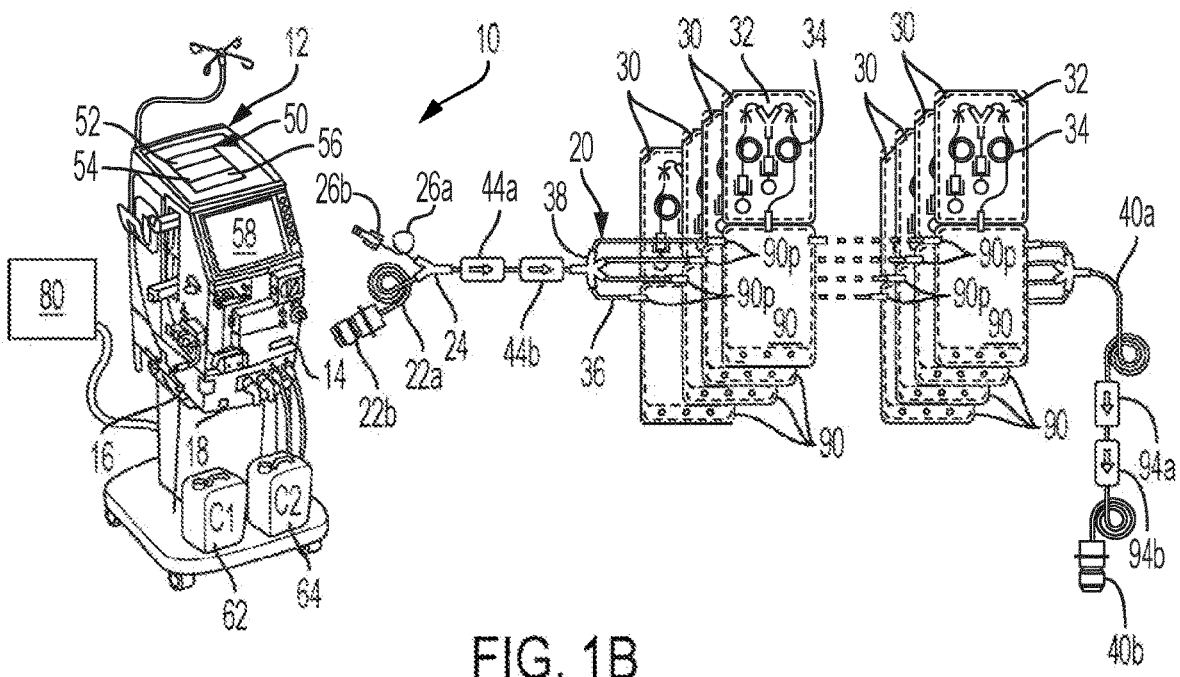
Figure 1C:
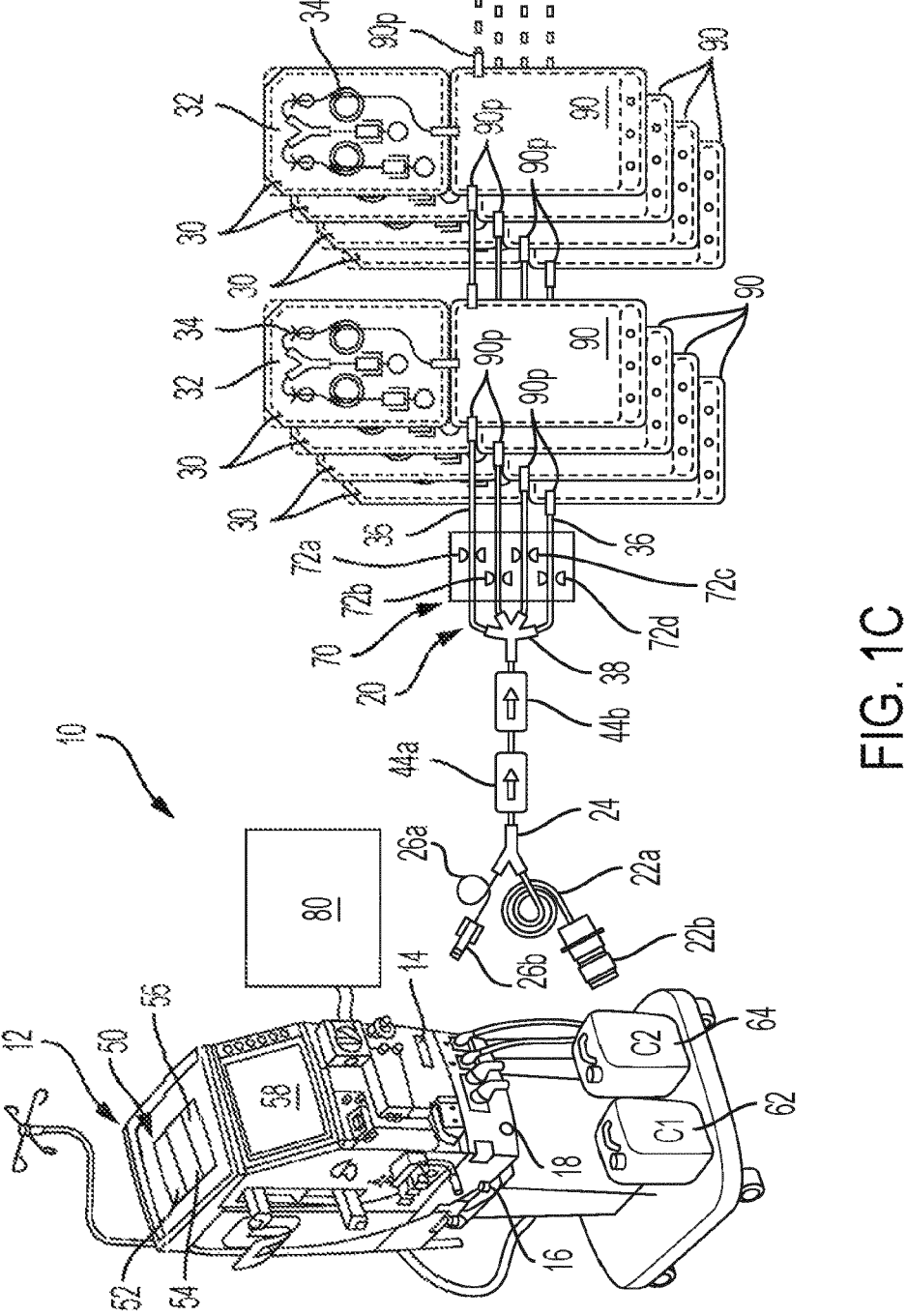

Referring now to the drawings and in particular to FIGS. 1A to 1C, an embodiment of a system 10 of the present disclosure, which uses a dialysis machine 12, such as an in-center dialysis machine to create dialysis fluid for peritoneal dialysis ("PD") is illustrated. FIGS. 1A to 1C illustrate that system 10 may include a central water purification station or standalone water purifier 80 that feeds a plurality of hemodialysis machines 12. Local water purification equipment may be used instead, such as any one or more of reverse osmosis ("RO"), ultraviolet ("UV") radiation, electrodeionization, ultrafiltration, ion-exchange resins, and/or heat disinfection. One suitable local water purifier has the product name WRO300H.

Hemodialysis machine 12 in FIGS. 1A to 1C includes at least one mixing pump for mixing purified water from central water purification station or standalone water purifier 80 with at least one concentrate 62, 64. Hemodialysis machine 12 in one embodiment includes a purified water pump that pulls purified water from central water purification station or standalone water purifier 80, such that central water purification station or standalone water purifier 80 may, but does not have to, supply its own water pressure. In an alternative embodiment, central water purification station or standalone water purifier 80 includes one or more pump that pumps purified water under positive pressure to hemodialysis machine 12. Here, hemodialysis machine 12 does not have to have a pump to pump purified water from central water purification station or standalone water purifier 80.

In any case, hemodialysis machine 12 includes pumps for mixing PD fluid and for delivering the dialysis fluid from the hemodialysis machine. In one embodiment, hemodialysis machine 12 of system 10 includes a first concentrate pump for metering an electrolyte concentrate (possibly containing a buffer) from container 62 into the purified water and a second concentrate pump for mixing glucose concentrate from a glucose concentrate container 64 with the mixture of purified water and electrolyte concentrate. One or more conductivity cell (or other type of composition sensor) is/are used in one embodiment to ensure the proper proportioning of buffer concentrate 62 with purified water and the mixture of buffer concentrate 62 and purified water with glucose concentrate 64. The conductivity readings may be temperature compensated. Hemodialysis machine 12 may also include a heater, such as an inline heater. The heater may (e.g., to promote mixing and/or for improved conductivity readings) or may not be energized during the preparation of the PD fluid for storage in containers or bags 90. Hemodialysis machine 12 also includes a pump, e.g., the fresh dialysis fluid pump of the machine, for delivering fresh (possibly heated) PD fluid at a desired or settable pressure and/or flowrate, e.g., 750 mm Hg or less and 300 to 800 mL/min, e.g., 500 mL/min. The pressure depends on the length of the overall tubing leading to PD fluid containers 90, wherein the containers do not add significantly to the required pressure until becoming full. Sterile sterilizing grade filters 44a, 44b add significantly to pressure drop and are therefore sized and numbered so as to provide an overall pressure drop that is within the capability of hemodialysis machine 12, e.g., 750 mm Hg or less.

It is contemplated for system 10 to mix purified water with the PD concentrates in a plurality of ways. In the above example, buffer (electrolyte) concentrate 62 is mixed first with purified water and a first conductivity reading is taken. That mixture is then mixed with glucose concentrate 64 and a final conductivity reading is taken. In an alternative embodiment, glucose concentrate 64 is mixed first with purified water and a first reading is taken via a glucose sensor, which may be a separate sensor coupled fluidly with hemodialysis machine 12 or integrated into the internal flowpath of the hemodialysis machine. That mixture is then mixed with buffer concentrate 62 and a final conductivity reading is taken. In a further alternative embodiment, the mixing of at least one of buffer concentrate 62 or glucose concentrate 64 is done on a volumetric basis, wherein precise amounts of at least one concentrate 62 and 64 is/are mixed with a precise amount of purified water.

It is contemplated to make hardware and software changes as needed to an existing hemodialysis machine 12 of system 10 for the production of PD fluid. Software changes are made in a control unit 50 of dialysis machine 12. Control unit 50 as illustrated includes one or more processor 52, one or more memory 54 and a video controller 56 for controlling user interface 58. The software changes may include, for example, establishing a dedicated container filling mode in which hemodialysis machine 12 runs at a specified pressure and flowrate for a known amount of time or metered amount of volume of PD fluid. The filling mode in an embodiment allows for different sizes and numbers of containers 90 to be filled, e.g., by prompting the operator to enter the size of container 90, e.g., two, four, five or six liters, and to enter the number of containers 90 to be filled in the filling sequence (one container or multiple ganged containers). From there, hemodialysis machine 12 calculates how much PD fluid is to be prepared for the next batch or filling sequence and delivers same to a tubing set, which includes one or more container 90, any tubing and connectors connecting two or more containers 90, and in one embodiment one or more terminal or sterile sterilizing grade filters 44a, 44b provided upstream of the containers.

The software updates may also include a confirmation in the filling mode from the operator that a filled one or more container 90 has been removed from hemodialysis machine 12 and that a new, empty and presterilized tubing set including one or more container 90 and one or more terminal or sterile sterilizing grade filters 44a, 44b have been loaded onto the machine. The confirmation may also ask the operator to confirm the number and volume of containers 90 of the new tubing set. Once confirmed, hemodialysis machine 12 in the filling mode enables the operator to press "start" to begin the next filling sequence.

Software updates may also include any updates needed to cause a label to be printed having any desired information, such as date that the PD fluid is prepared, time that the PD fluid is prepared, expiration period or date, type or formulation of the PD fluid, quantity of the PD fluid, and machine identification that prepared the PD fluid, operator identification, and/or lot number. Hardware changes may again include a label printer 14 provided with hemodialysis machine 12 as illustrated in FIGS. 1A to 1C. In an alternative embodiment, label printer 14 is provided separately from hemodialysis machine 12. Hardware changes may also include the provision of a hanger or holder 16 positioned and arranged to hang or otherwise hold one or more container 90 of dialysis fluid. Hanger or holder 16 may for example be one or more safety clamp provided by hemodialysis machine 12.

Software updates may further include updates needed to control a remote, standalone valve station discussed in connection with FIG. 1C. The standalone valve station selectively opens and closes the filling lines leading to the PD fluid containers. Hemodialysis machine 12 may here be programmed to tell the standalone valve station which valves to open and when. Hemodialysis machine 12 is also programmed to coordinate PD fluid delivery with the valve sequencing of the standalone valve station.

FIG. 1A illustrates that in one embodiment, multiple containers 90 are filled with PD fluid in a single filling sequence. In the illustrated embodiment, containers 90 are provided as part of a large overall presterilized tubing set 20. Any portion of tubing set may be formed from any one or more plastic, e.g., polyvinylchloride ("PVC") or a non-PVC material, such as polyethylene ("PE"), polyurethane ("PU") or polycarbonate ("PC"). Tubing set 20 includes an inlet line

22a having an inlet line connector 22b. Inlet line connector 22b may be configured to connect to a dialysis fluid outlet port (not illustrated) of hemodialysis machine 12 or to a dialysis fluid outlet line (not illustrated) extending from hemodialysis machine 12. Inlet line 22a connects via a Y or T connection 24 to a pressure transmission line 26a having a pressure transmission line connector 26b. Pressure transmission line connector 26b plugs into a pressure transducer port 18 of hemodialysis machine 12. Fluid pressure within pressure transmission line 26a is transmitted to a pressure transducer via pressure transducer port 18.

In one embodiment, control unit 50 looks at multiple pressure readings over the course of a filling procedure to determine when containers 90 have been filled to a desired level. Here, control unit 50 may take a first pressure reading after an initial filling amount, e.g., 100 mL, of dialysis fluid is delivered to containers 90. This reading may be taken by momentarily stopping the filling so that the pressure measured is a static pressure. Then, filling is resumed and a second pressure measurement is taken immediately to record a corresponding dynamic pressure, which reflects the pressure drop caused by tubing set 20, including sterile sterilizing grade filters 44a and 44b. Control unit 50 may then take multiple dynamic readings over time, that is, without stopping flow, to monitor how the pressure changes due a changing flow resistance provided by sterile sterilizing grade filters 44a and 44b. Control unit 50 then waits until a time when it is expected that containers 90 are becoming close to being full based on a known flowrate and total volume of containers 90 and stops flow again to take an additional static pressure reading via the pressure transducer. If a change in static pressure equals or exceeds a characteristic change known to control unit 50 to correspond to a container full condition, then the control unit stops the filling and notifies the operator that containers 90 are full and ready to be removed. If a change in static pressure does not meet a characteristic change known to control unit 50 to correspond to a container full condition, then the control unit resumes filling either for a preset period of time, or for a calculated period of time expected to meet or exceed the characteristic change in static pressure. Control unit 50 stops flow again after the preset or calculated amount of time to take an additional static pressure reading from the pressure transducer. Control unit 50 repeats the above loop until the change in static pressure equals or exceeds a characteristic change.

The above structure and method for determining a container full condition operates so that the operator does not have to enter, and control unit 50 does not have to know, the number and volume of containers 90. The filling sequence is nevertheless stopped automatically so that the operator does not have to monitor visually or time the filling of containers 90.

One or more final terminal or sterile sterilizing grade filters 44a, 44b is/are located downstream of Y or T connection 24 as illustrated in FIGS. 1A to 1C. Terminal or sterile sterilizing grade filters 44a, 44b in combination with the purification provided by central water purification station or standalone water purifier 80 provide a purity for the PD fluid suitable for delivery into the patient's peritoneal cavity. One final terminal or sterile sterilizing grade filter 44a or 44b may be sufficient to provide the necessary purity, however, two or more of such filters provide redundancy in case one of the filters becomes compromised. In an embodiment, terminal or sterile sterilizing grade filter 44a or 44b are sized and configured for the number of containers 90 provided with tubing set 20. Pore sizes for the sterile sterilizing grade filters 44a and 44b may, for example, be less than a micron, such as 0.1 or 0.2 micron. Suitable sterile sterilizing grade filters 44a and 44b may, for example, be Pall IV-5 filters, be Yukon3 filters, or be filters provided by the assignee of the present disclosure.

Where two sterile sterilizing grade filters 44a and 44b are provided, e.g., in FIGS. 1A to 1C, system 10 likely does not need to perform an integrity check due to the redundancy. For either system 10 or 110 (FIG. 2), however, it is contemplated to test the integrity of a terminal or sterile sterilizing grade filter 44a or 44b, especially when only one is provided (however the test may still be applied to two filters). System 10 or 110 wets the filter by driving PD fluid (system 10) or concentrate solution (system 110) through and past the filter 44a and/or 44b. System 10 or 110 drives enough PD fluid or solution past the filter, so that after the air integrity test, the PD fluid or solution can be pulled back to dialysis machine 12 to remove all air from the filter 44a and/or 44b to an air collection device or vent of dialysis machine 12. Then, dialysis machine 12 operates the dialysis fluid pump to pump air in the line leading to filter 44a and/or 44b until air reaches the filter, at which point the air cannot proceed through a wetted and intact filter. Control unit 50 then causes an air pressure to be built and monitored in the line leading to filter 44a and/or 44b. If the pressure holds, the filter is deemed to be intact. If a pressure decrease is sensed, control unit 50 deems the filter to be compromised and prompts the operator to discard the entire tubing set. When the filter (upstream filter if two are provided) is deemed to be intact, hemodialysis machine 12 using the dialysis fluid pump applies a negative pressure in the line leading to filter 44a and/or 44b, pulling the dialysis fluid (system 10) or concentrate solution (system 110) residing downstream from the filter, back through the filter and the line, pushing the air in an upstream direction to the air collection device or vent of machine 12. Dialysis fluid filling may then proceed as described herein, with the line leading to filter 44a and/or 44b primed with PD fluid or concentrate solution.

As illustrated in FIG. 1A, it is contemplated for overall tubing set 20 to include treatment tubing sets 30, which are eventually separated from each other, each set 30 located downstream from terminal or sterile sterilizing grade filters 44a, 44b and each including a container 90 and an overpouch 32 housing PD patient tubing 34. In an alternative embodiment, overpouch 32 additionally covers container 90. PD patient tubing 34 may be configured for manual or Continuous Ambulatory Peritoneal Dialysis ("CAPD") or for operation with a peritoneal dialysis cycler for automated peritoneal dialysis ("APD") or for other sterilized fluid applications, such CRRT treatments and saline or NaCl fluid deliveries. In an embodiment, overall tubing set 20 is presterilized (e.g., via gamma radiation, ethylene oxide or steam) with treatment tubing sets 30 ganged via filling tubes 36 as illustrated in FIG. 1A.

FIG. 1A illustrates that filling tubes 36, a manifold connector 38 and connecting ports 90p provided on containers 90 enable the containers to be ganged in series, in parallel or in both series and parallel. While two columns of four containers 90 are illustrated in FIG. 1A, it is contemplated to instead provide three or more columns of containers. As discussed herein, the series and/or parallel filling of containers 90 may be performed via control unit 50 (*i*) causing hemodialysis machine 12 to meter an amount of fresh PD fluid based on the number and volume of containers 90 or (ii) detecting a characteristic static pressure change (discussed above) indicating that each of the containers 90 has been filled.

Depending on the number of containers 90 provided with overall tubing set 20, it is contemplated to hang or otherwise place containers 90 (perhaps only a single container) on a hanger, infusion fluid pole or other type of holder 16 of hemodialysis machine 12. Alternatively, overall tubing set 20 may be supported by a rack (not illustrated) located adjacent to hemodialysis machine 12. Hemodialysis machine 12 and/or the rack may then be provided with a heat sealer or tube welder (illustrated in FIG. 2) for heat sealing filling tubes 36 leading to container ports 90p closed. Once the filling tubes 36 are heat sealed closed, the filling tubes 36 may be cut with scissors or perhaps separated by the heat sealing, allowing tubing sets 30 with their filled containers to be separated from one another. Filling tubes 36 leading to container ports 90p may alternatively be mechanically clamped, cut and capped for sterile separation from each other.

FIG. 1B illustrates that overall tubing set 20 of system 10 may further include a return line 40a and return line connector 40b for allowing PD fluid samples to be returned to hemodialysis machine 12 for testing. In the illustrated embodiment, return line may have one or more terminal or sterile sterilizing grade filters 44a or 44b, which prevent(s) any backflow in return line 40a from potentially contaminating the PD fluid contained within containers 90. The testing of the fluid at hemodialysis machine 12 may involve any desired form of testing, e.g., any one or more of further conductivity testing, sample removal for microbial, e.g., colony forming unit ("CFU"), testing or chlorine testing.

In particular, one suitable hemodialysis machine for system 10 is an AK 98™ hemodialysis machine produced by the assignee of the present disclosure, which provides a conductivity sensor positioned in a used dialysis fluid path leading to drain. That conductivity sensor may be used to ensure that the PD fluid samples have the same (or within an allowed margin of error) conductivity as an expected conductivity. In one embodiment, return line 40a is connected to a dialyzer outlet line of hemodialysis machine 12, wherein the dialyzer outlet line is the reusable tubing provided with hemodialysis machine 12 that is normally connected to an outlet of the dialyzer (for a hemodialysis treatment). The operator then commands hemodialysis machine 12 to suck a sample from containers 90 via return line 40a and send the sample past the conductivity sensor to perform a test measuring the conductivity of the sample. In an embodiment, the sensed conductivity is displayed by hemodialysis machine 12 for the operator to view and either confirm the batch of filled PD fluid containers 90 if the reading is good or discard the batch if the reading is outside of acceptable limits. In another embodiment, hemodialysis machine 12 is programmed to alarm if the sensed conductivity is outside of the acceptable limits. Otherwise, the filled containers may be assumed to be acceptable.

Assuming the test sample volume to be small, e.g., 100 mL or less, the time needed for hemodialysis machine 12 to transport the sample to the conductivity sensor will be short. Here, there is a very low risk that bacteria may enter the system via the return line 40a and thus one or more terminal or sterile sterilizing grade filter 44a or 44b in FIG. 1B may not be needed. Nevertheless, it may be desirable as an extra safety precaution to provide such one or more filter as illustrated in FIG. 1B.

If hemodialysis machine 12 is not equipped with a conductivity sensor that is accessible, system 10 may instead use an external conductivity sensor and alarm and/or readout. PD fluid system 10 may also include an external glucose sensor to confirm the glucose level of filled PD fluid containers 90.

FIG. 1C illustrates that system 10 may further include or provide a standalone valve station 70, e.g., removeably fixed to the rack holding overall tubing set 20. Valve station 70 includes valves 72a to 72d, e.g., a valve for each filling tube 36. While four valves are illustrated, any number of valves may be provided depending on the number of filling lines to be opened and closed. Valves 72a to 72d in an embodiment are electrically opened, de-energized closed solenoid pinch valves. Valve station 70 in an embodiment includes power equipment (not illustrated) for supplying power to valves 72a to 72d. Valve station 70 may also include a small microcontroller (not illustrated) for controlling when power is supplied to which valves 72a to 72d. In an embodiment, the microcontroller includes a transceiver that operates wirelessly, e.g., via Bluetooth or WiFi, with a transceiver associated with control unit 50 of hemodialysis machine 12 (or could operate in a wired manner, e.g., via Ethernet). In such an embodiment, control unit 50 of hemodialysis machine 12 commands microcontroller 254 of valve station 70 to sequence valves 72a to 72d in a desired manner. For instance, control unit 50 of hemodialysis machine 12 commands the microcontroller to sequence valves 72a to 72d such that the front row of containers 90 is filled first, followed by the second row, then the third row, then the bottom row. The completion of the filling of each row may be via a known amount of PD fluid delivered based on number and volume of containers 90 in each row or via a sensed characteristic static pressure change as discussed herein.

Control unit 50 is in one embodiment programmed to control the mixing of concentrates and purified water at the same time as controlling valves 72a to 72d of valve station 70 so as to allow different containers 90 in tubing set 20 to be filled with different formulations or fluids of different chemical constituencies. With PD, for example, control unit 50 may be programmed to produce different glucose concentrations in different containers 90. Here, system 10 may create a set of containers 90 that hold different fluids that are, for example, individualized for a specific patient according to the patient's prescription. Control unit 50 of hemodialysis machine 12 is programmed to create the prescribed set of filled containers 90 for the patient. In one PD example, system 10 fills three PD containers 90 with a low glucose PD fluid (by opening valves 72a to 72c one at a time for the three containers) and a fourth PD container with a higher glucose level fluid (by opening valve 72d), wherein the patient's prescription calls for all four containers to be used in a single treatment, for example, the three low glucose containers used first followed by the higher glucose container as a last treatment fill.

Figure 2:
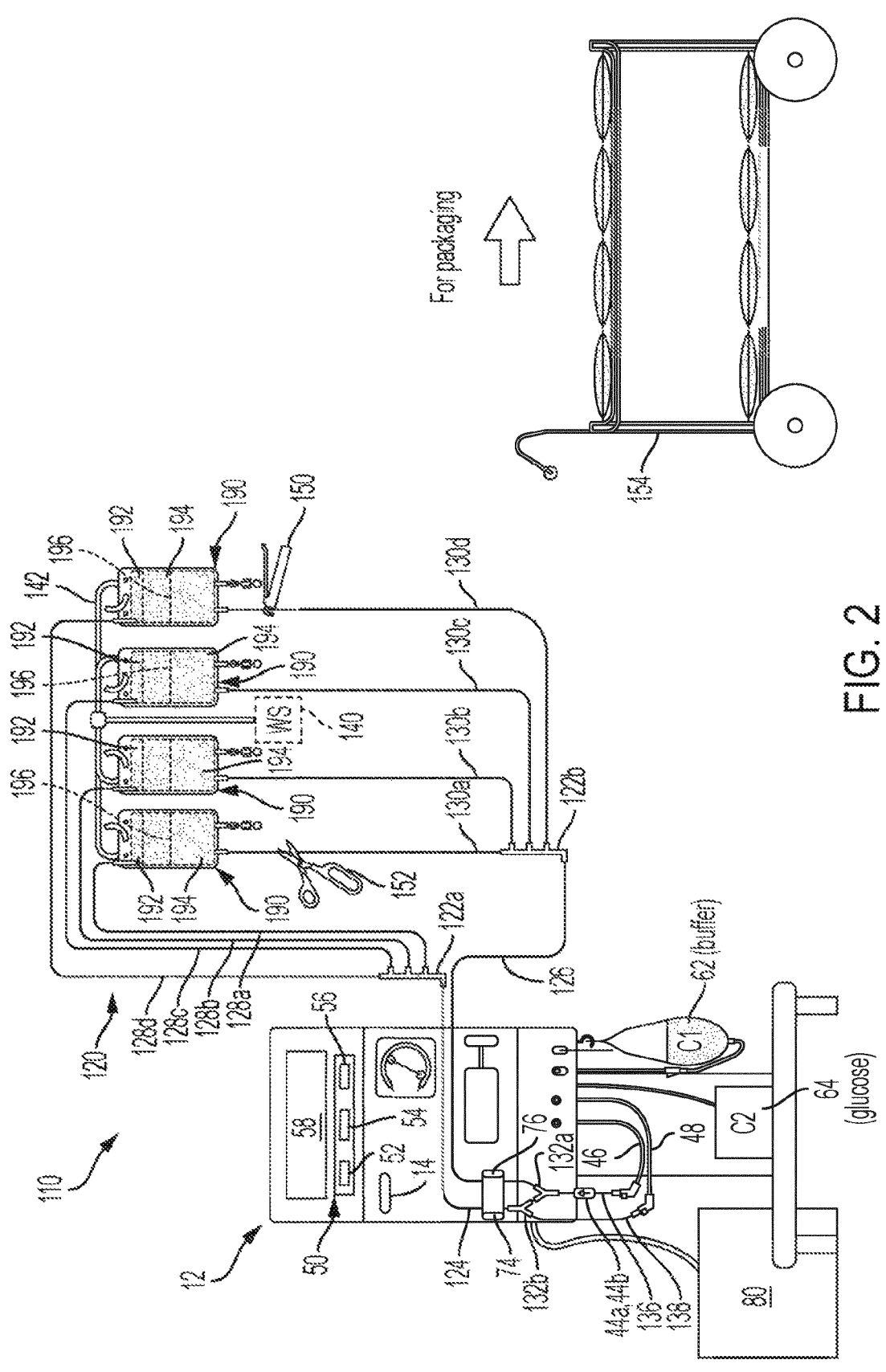

In an alternative embodiment, if only two valves are needed, two clamps provided on the outside of hemodialysis machine 12 may be used instead (see, e.g., clamps 74 and 76 of FIG. 2). The dialysis machine clamps are programmably opened and closed via control unit 50. Here, manifold connector 38 splits into two filling tubes 36, each of which is selectively opened and closed via one of the automated machine clamps.

It is also contemplated for the transceiver operable with control unit 50 of mixing device or hemodialysis machine 12 in either system 10 or 110 (FIG. 2) to communicate wired or wirelessly via a network with an inventory tracking system that logs the number, time and date of fresh dialysis fluid containers 90 prepared and the raw materials consumed. The inventory tracking system may be accessed to know how many containers 90 having differing expiration dates have been produced and at what location, e.g., hospital or clinic. The inventory tracking system may also identify raw materials that need to be ordered and delivered and in one embodiment places such orders automatically.

Referring now to FIG. 2, an alternative embodiment of a system 110 of the present disclosure, which uses an in-center dialysis machine to create PD dialysis fluid component solutions for a final PD fluid is illustrated. The primary difference with system 110 is that a final PD fluid is not created, instead PD fluid concentrate component solutions are created and stored in containers for final mixing at the time of use. FIG. 2 illustrates that system 110, like system 10, may include a central water purification station or standalone water purifier 80 that feeds a plurality of hemodialysis machines 12 (local water purification equipment described for system 10 may be used in system 110 alternatively). Hemodialysis machine 12 in FIG. 2 includes all of the structure and functionality discussed above for mobile systems 10. In particular, hemodialysis machine 12 includes at least one mixing pump for mixing purified water from central water purification station or standalone water purifier or standalone water purifier 80 with at least one concentrate 62, 64. Hemodialysis machine 12 in one embodiment includes a purified water pump that pulls purified water from central water purification station or standalone water purifier 80, such that central water purification station or standalone water purifier 80 may, but does not have to, supply its own water pressure. In an alternative embodiment, central water purification station or standalone water purifier 80 includes one or more pump that pumps purified water under positive pressure to hemodialysis machine 12. Here, hemodialysis machine 12 does not have to have a pump to pump purified water from central water purification station or standalone water purifier 80.

In any case, hemodialysis machine 12 includes pumps for mixing PD fluid and for delivering the dialysis fluid from the hemodialysis machine. In one embodiment, hemodialysis machine 12 of system 110 includes a first concentrate pump for metering buffer (or electrolyte) concentrate from a buffer concentrate container 62 into the purified water and a second concentrate pump for mixing glucose concentrate from a glucose concentrate container 64 into the purified water. One or more conductivity cell is/are used in one embodiment to ensure the proper proportioning of buffer concentrate 62 with purified water and the proportioning of glucose concentrate 64 with purified water. The conductivity readings may be temperature compensated. Hemodialysis machine 12 may also include a heater, such as an inline heater. The heater may (e.g., to promote mixing and/or for improved conductivity readings) or may not be energized during the preparation of the PD fluid concentrates for storage in alternative dual chamber containers or bags 190.

Hemodialysis machine 12 also includes a pump, e.g., the fresh dialysis fluid pump of the machine, for delivering the fresh (possibly heated) PD fluid component solutions at a desired or settable pressure and/or flowrate, e.g., the same as system 10, or 750 mm Hg or less and 300 to 800 mL/min, e.g., 500 mL/min. The pressure depends on the length of the overall tubing leading to containers 190, wherein the containers do not add significantly to the required pressure until becoming full. One or more sterile sterilizing grade filters 44a, 44b add significantly to pressure drop and is/are therefore sized and numbered so as to provide an overall pressure drop that is within the capability of hemodialysis machine 12, e.g., 750 mm Hg or less.

System 110 is provided with two or more concentrates, labeled generally as C1 and C2. Concentrates C1 and C2 may be concentrates for producing any type of sterilized medical fluid discussed herein, such as PD fluid, any type of continuous renal replacement treatment ("CRRT") fluid including HD fluids, substitution or replacement fluids for hemofiltration ("HF") and hemodiafiltration ("HDF"), saline, lactated ringers and other NaCl solutions. For ease of description, system 110 is described for PD fluids, wherein Concentrate C1 is a buffer concentrate and concentrate C2 is a glucose concentrate.

System 110 is provided with an alternative large overall tubing set 120, which includes alternative containers 190. Any portion of tubing set 120 may be formed from any one or more plastic, e.g., polyvinylchloride ("PVC") or a non-PVC material, such as polyethylene ("PE"), polyurethane ("PU") or polycarbonate ("PC"). Tubing set 120 includes two manifolds 122a and 122b, one each for the solutions formed from concentrates 62 and 64. A C1-concentrate manifold line 124 carries a combination of C1-concentrate (buffer) and purified water from hemodialysis machine 12 to manifold 122a. A C2-concentrate manifold line 126 carries a combination of C2-concentrate (glucose) and purified water from hemodialysis machine 12 to manifold 122b. C1-concentrate manifold line 124 and C2-concentrate manifold line 126 may be connected via Y or T-connectors 132a and 132b as illustrated, e.g., for priming purposes, and to flush reusable supply line 46, after having filled first compartment 192 with a first concentrate solution, with a second concentrate solution that is later filled into second compartment 194. The flush is performed to drain via drain line 48.

Manifold lines 124 and 126 and their respective concentrates are controlled independently via outer automated machine clamps 74 and 76, respectively, wherein the automated machine clamps 74 and 76 are under control of control unit 50 having one or more processor 52, one or more memory 54 and a video controller 56 for controlling user interface 58.

Manifold lines 124 and 126 of disposable set 120 in the illustrated embodiment connect via Y-connector 132a and disposable supply line 136 to reusable supply line 46 of hemodialysis machine 12 having a reusable connector, where supply line 46 may be the reusable fresh dialysis fluid line normally connected to a dialyzer for treatment. A disposable drain line 138 connects to a reusable connector of reusable drain line 48 of machine 12, where drain line 48 may be a reusable used dialysis fluid line normally connected to the dialyzer. After the filling of alternative containers 190 and the removal of disposable set 120 from reusable lines 46 and 48, the reusable connectors of reusable lines 46 and 48 may be plugged into dedicated docking stations of hemodialysis machine 12 or be connected together, after which a short disinfection cycle, e.g., via heated purified water, may be performed while a next disposable set 120 is installed for a next fill.

Fill lines 128a to 128d lead from manifold 122a to a C1-concentrate solution chamber 192 of each of dual chamber containers or bags 190. While four fill lines 128a to 128d are illustrated, any desired number of fill lines 128n may be provided alternatively. Fill lines 130a to 130d lead from manifold 122b to a C2-concentrate solution chamber 194 of each of dual chamber containers or bags 190. Again, while four fill lines 130a to 130d are illustrated, any desired number of fill lines 130n may be provided alternatively, wherein 130n equals 128n.

In any desired order, hemodialysis machine 12 of system 110 under control of control unit 50 mixes C1-concentrate (buffer) from C1-concentrate source 62 with purified water in a desired ratio and delivers a desired amount of the solution to the C1-concentrate solution chamber 192 of each of dual chamber container or bag 190. Hemodialysis machine 12 of system 110 under control of control unit 50 mixes C2-concentrate (glucose) from C2-concentrate source 64 in a desired ratio and delivers a desired amount of the solution to the C2-concentrate solution chamber 194 of each of dual chamber container or bag 190. Chambers 192 and 194 in one embodiment are separated by a frangible seal 196, which a nurse, clinician or patient opens at the time of use to allow the C1-concentrate solution and the C2-concentrate solution to mix together to form an overall PD fluid for treatment. The volume of the finally mixed PD fluid is any desired amount, e.g., two, four, five or six liters.

It should be appreciated that system 110 is fully capable of pumping two concentrate solutions into a single chamber 192 or 194, which may for example be mixed with purified water. So, for example, three concentrates may be provided to produce any medical fluid discussed herein, wherein a first concentrate solution formed from the first concentrate is delivered to chamber 192, while second and third concentrate solutions formed from the second and third concentrates, respectively, are delivered to chamber 194.

The volumes of the C1-concentrate solution and the C2-concentrate solution delivered to chambers 192 and 194, respectively, need to be relatively precise. It is accordingly contemplated to use an accurate dialysis fluid pump of hemodialysis machine 12, e.g., a piston pump, or a less accurate dialysis fluid pump, e.g., a gear pump, in combination with one or more flowmeter outputting to control unit 50. Here, control unit 50 is programmed to pump the needed volumes of C1-concentrate (buffer) solution and the C2-concentrate (glucose) solution and to stop pumping and close clamps 74 and 76 when the programmed volumes are reached. Alternatively, an optional weigh scale 140 may be provided to weigh containers or bags 190 as they hang from a multi-unit hanger or holder 142. Weigh scale 140 outputs wired or wirelessly to control unit 50, which is programmed to stop pumping and close clamps 74 and 76 when the programmed C1-concentrate or buffer solution weight and the C2-concentrate or glucose solution weight are reached.

Chambers 192 and 194 are sized to contain a volume of a particular concentrate solution, such that when the concentrate solutions are mixed after frangible seal 196 is ruptured, the resulting overall medical fluid has and meets a defined concentration for one or more chemical constituent. In a PD example, a 1.36% glucose ready to use PD fluid may have a sodium chloride concentration of 5.38 g/L and an equivalent to anhydrous glucose concentration of 13.6 g/L. Chambers 192 and 194 are then sized to hold a volume and concentration of buffer and glucose solutions that when mixed meet the above concentrations. In one example, to create one liter of 1.36% glucose ready to use PD fluid having the above final concentrations, chamber 192 is sized to hold 637.5 ml of a buffer solution having a sodium chloride concentration of 8.43 g/L, while chamber 194 is sized to hold 362.5 ml of a glucose solution having an equivalent to anhydrous glucose concentration of 37.5 g/L. Here, control unit 50 is programmed to create such buffer and glucose solutions by adding purified water to concentrates C1 and C2, respectively, and to deliver the specified volumes of the solutions to compartments 192 and 194.

System 110 of FIG. 2 also illustrates structure and functionality for separating any of the containers or bags 90 or 190 discussed herein from the remainder of a disposable set, here disposable set 120. In FIGS. 1A to 1C, the structure and functionality described here could be used to separate containers or bags 90 from overall tubing or disposable set 20. The structure includes a handheld heat sealer 150, which may for example be a Sebra® 1105 Heat Sealer, which seals closed both fill lines 128a to 128d and fill lines 130a to 130d. If needed, each fill line may be sealed two or more times for extra security. After sealing, each of fill lines 128a to 128d and 130a to 130d may be clamped below the heat seal(s) to prevent spillage, e.g., via a Roberts™ clamp, and then cut via scissors 152 between heat seal(s) and the clamps or between heat seals. One possible solution to avoid mechanical clamps is to make three heat seal welds and to cut between the second and third welds counting from container 90 or 190. The first and second welds remain for increased security.

The separated containers or bags 190 may then be labeled via a label printed at label printer 14 of hemodialysis machine 12 or via a separate label printer, wherein the label may include any of the information discussed herein. Once separated containers or bags 190 are labeled, they may be loaded onto a cart 154 and, for example, transported to a packaging area where the containers are packaged for delivery to a PD patient's home for treatment or use at a hospital or clinic.

The dual chamber containers or bags 190 having separate C1- and C2-PD concentrate solutions have a potentially longer shelf life than containers or bags 90 holding a finally mixed PD fluid, which may be a month or longer. The finally mixed fluid may precipitate over time, leading to a shorter shelf life. Containers or bags 190 promote the possibility of using bicarbonate, or a mixture of bicarbonate and lactate, as a buffer concentrate. It is also contemplated to place container of bag 190 in an overpouch, which helps to prevent degradation of the two or more separated solutions.

There are a number of alternative embodiments for tubing set 120. In a first alternative embodiment, at least one sterile sterilizing grade filter 44a, 44b is moved so that a first at least one sterile sterilizing grade filter 44a, 44b is located in any desired location along manifold line 124 and a second at least one sterile sterilizing grade filter 44a, 44b is located in any desired location along manifold line 126. In a second alternative embodiment, Y or T-connector 132b is moved upstream of sterile sterilizing grade filter 44a, 44b, so that any contamination formed via the connection of disposable drain line 138 to reusable drain line 48 is removed via downstream sterile sterilizing grade filter 44a, 44b. It should be appreciated that for any version of tubing set 120 discussed herein, a clamp or valve located inside hemodialysis machine 12 and under control of control unit 50 opens or occludes reusable drain line 48 to allow or not allow fluid to flow back down disposable drain line 138 via Y or T-connector 132b.

Figure 3:
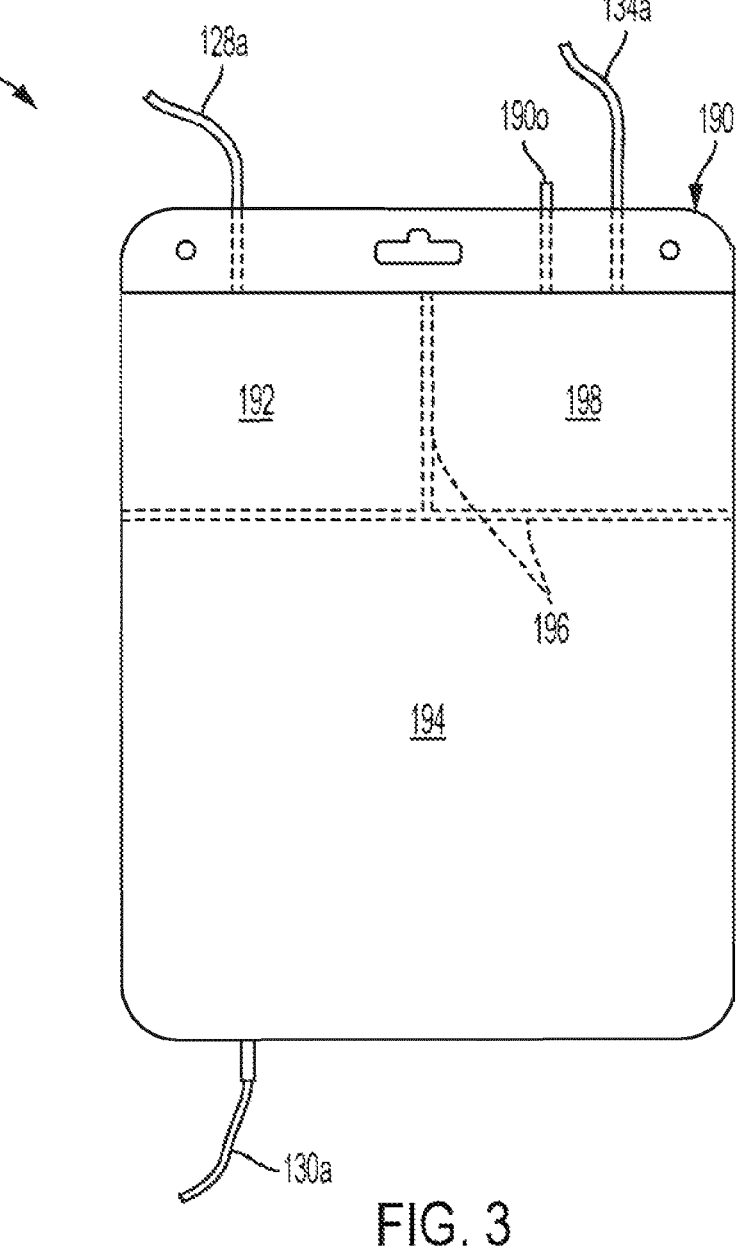
FIG. 3 is a top plan view of an alternative implementation of a multi-chamber container or bag of the present disclosure.

Referring now to FIG. 3, an alternative multi-chamber container 190 for use with system 110 is illustrated, and which may be made of any of the materials discussed herein. Alternative multi-chamber container 190 includes chambers 192 and 194 for receiving C1-concentrate solution and C2-concentrate solution, respectively, as has been described herein. Alternative multi-chamber container 190 includes at least one additional chamber 198, wherein all three chambers 192, 194 and 198 are separated by frangible seal 196. Fill line 128a feeds C1-concentrate solution to chamber 192, while fill line 128b feeds C2-concentrate solution to chamber 194 as has been discussed herein.

It is contemplated for system 110 to use at least one additional chamber 198 in a plurality of ways, each under control of control unit 50. In the illustrated embodiment, a third fill line 134a is placed in fluid communication with at least one additional chamber 198 so that hemodialysis machine 12 is able to fill chamber with a third C3-concentrate solution. If hemodialysis machine 12 includes only two external clamps 74 and 76, then standalone valve station 70 described in connection with FIG. 1C may be employed to control third fill line 134a or all three fill lines 128a, 130a and 134a. The proportioning and volumetric control of a third C3-concentrate solution to additional chamber 198 may be performed via any of the structures and methods described herein.

Additional chamber 198 may for example hold a second glucose solution, which is mixed with the first glucose solution from chamber 194 and buffer solution from chamber 192 to form a ready to use PD fluid when frangible seal 196 is ruptured. Additional chamber 198 may also be used to receive an additional solution for mixing to form any type of continuous renal replacement treatment ("CRRT") fluid including HD fluids, substitution fluids for hemofiltration ("HF") and hemodiafiltration ("HDF"), saline, lactated ringers and other NaCl solutions.

Three chamber container 190 may accordingly operate with a third C3-concentrate or with only two concentrates C1 and C2, wherein a first one of the concentrates is proportioned differently with purified water to produce different solutions of the one concentrate for filling two of the three chambers. The second concentrate is then proportioned to produce a desired second concentrate solution for filling the third chamber.

In an alternative embodiment, additional chamber 198 is prefilled with a desired solution and sterilized along with overall tubing set 120. Here, third fill line 134a is not needed. In the PD fluid example above, additional chamber 198 may be prefilled with a second glucose solution, which is mixed with the first glucose solution from chamber 194 and buffer solution from chamber 192 to form a ready to use PD fluid when frangible seal 196 is ruptured. Additional prefilled and presterilized chamber 198 may also be used to hold an additional solution for mixing to form any type of continuous renal replacement treatment ("CRRT") fluid including HD fluids, substitution fluids for hemofiltration ("HF") and hemodiafiltration ("HDF"), saline, lactated ringers and other NaCl solutions.

Container 190 in FIG. 3 includes an outlet port 190o for allowing the finally mixed fluid to be fluidly communicated for treatment.

Figure 4:
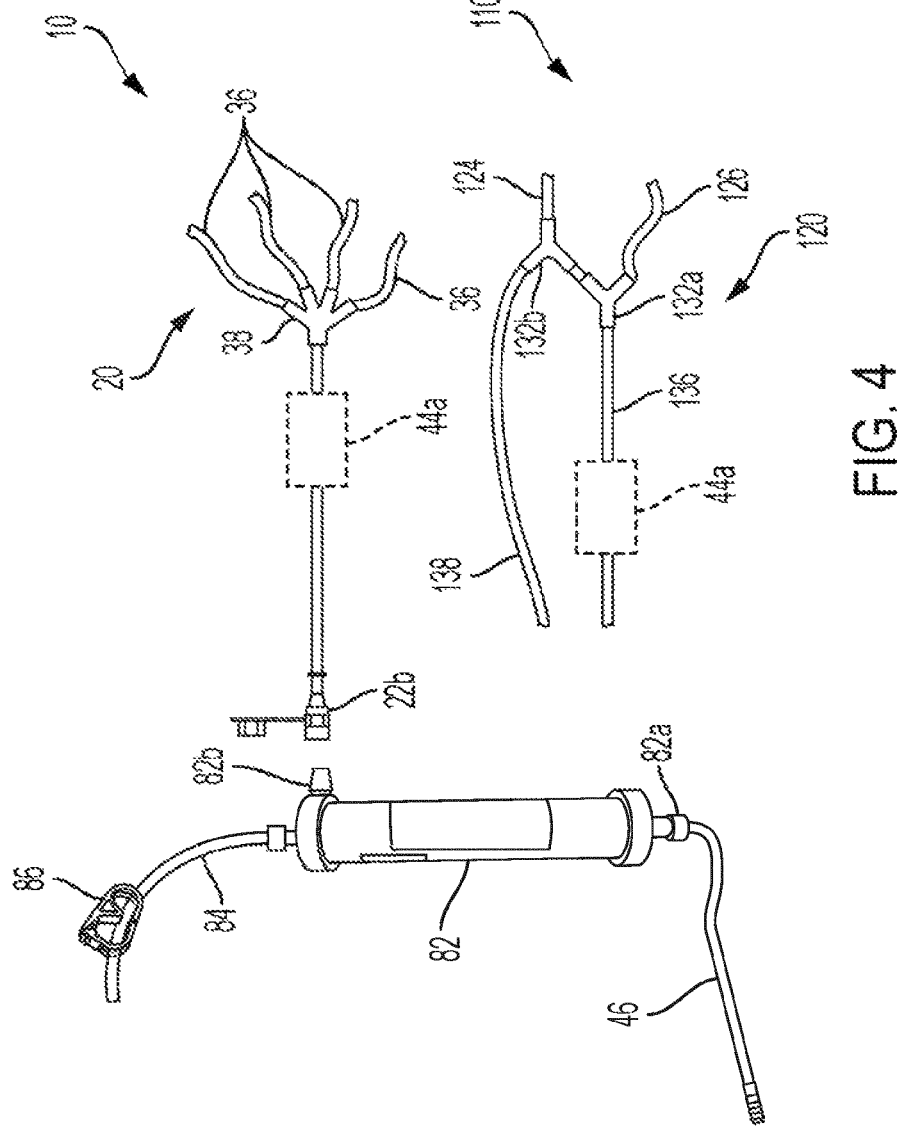
FIG. 4 is a front elevation view of an alternative embodiment for the systems described herein using a reusable ultrafilter or dialyzer.

Referring now to FIG. 4, an alternative implementation for systems 10 and 110 is illustrated. Systems 10 and 110 provide presterilized tubing sets 20 and 120, respectively, as discussed herein and rely on one or more sterile, sterilization filters 44a and 44b to place the medical fluids (system 10) or component solutions (system 110) in a sterilized condition for patient use. FIG. 4 adds a reusable filter 82, which may be an ultrafilter or a dialyzer, which in one embodiment is mounted to hemodialysis machine 12. In the illustrated embodiment, reusable filter 82 is an ultrafilter having an inlet port 82a that receives medical fluids or component solutions from hemodialysis machine 12, and a reject port to which a short, e.g., less than twelve inches (30.5 cm), priming line 84 is connected to allow reusable filter 82 to be primed after which priming line 84 is clamped closed via mechanical clamp 86. Ultrafilter 82 also includes an outlet port 82b that outputs further purified medical fluids or component solutions to presterilized tubing sets 20 and 120, respectively.

FIG. 4 illustrates how reusable filter 82 interacts differently with systems 10 and 110. In system 10, inlet line connector 22b of tubing set 20 instead of connecting to an outlet port or reusable supply line of hemodialysis machine 12, as discussed in connection with FIGS. 1A to 1C, connects here to the outlet port of reusable filter 82. Tubing set 20 may still provide one or more a sterile sterilizing grade filters 44a, 44b (shown optionally in phantom line), which further sterilize the medical fluid and protect against any contamination formed due to the connection of connector 22b to reusable filter 82. Further sterilized fluid exiting one or more sterile sterilizing grade filters 44a, 44b flows via to manifold connector 38 and filling tubes 36 to containers or bags 90 as described herein.

In system 110, disposable line 136 of tubing set 120 instead of connecting to a reusable supply line 46 of hemodialysis machine 12, as illustrated in FIG. 2, connects here to the outlet port of reusable filter 82. Reusable supply line 46 in FIG. 4 connects instead to the inlet port of reusable filter 82. Tubing set 120 may still provide one or more a sterile sterilizing grade filters 44a, 44b (shown optionally in phantom line), which further sterilize the medical fluid and protect against any contamination formed due to the connection of disposable line 136 to reusable filter 82. In FIG. 4, disposable drain line 138 still connects to reusable drain line 48 as illustrated in FIG. 2. Further sterilized fluid exiting one or more sterile sterilizing grade filters 44a, 44b flows via Y or T-connectors 132a and 132b, manifold lines 124 and 126, and fill lines 128a to 128n and 130a to 130n to containers or bags 190 as described herein.

FIG. 4 illustrates that alternative or additional reusable filtration may be added to the presterilized tubing sets 20 and 120 of systems 10 and 110, respectively. It is also expressly contemplated to package ultrafilter or dialyzer 82, reusable supply line 46 and priming line 84 assembled and sterilized in a first package and to package either tubing set 20 including all of its structure discussed herein assembled and sterilized in a second package or tubing set 120 including all of its structure discussed herein assembled and sterilized in the second package.

It is also contemplated to alternatively provide prefilled buffer and glucose chambers for PD systems 10 and 110 and to instead supply sterilized or purified water to an initially empty, e.g., the largest chamber. When the one or more frangible seal is broken, the concentrates mix with the sterilized or purified water to form PD fluid. Here, (i) the amount and concentration of the one or more concentrate and (ii) the amount and formulation of the dialysis fluid or the amount of sterilized or purified water are selected to provide a desired volume and overall formulation of PD fluid. Providing separate prefilled and sterilized concentrate chambers may again be desirable, for example, to increase shelf life of a filled container 90.

It should be understood that various changes and modifications to the presently preferred embodiments described herein will be apparent to those skilled in the art. It is therefore intended that such changes and modifications be covered by the appended claims.

The invention claimed is:

1. A tubing set for use with a machine that generates a medical fluid, the tubing set comprising:
  a line for connecting to the machine or to a fluid carrying structure extending from the machine;
  a Y or T-connector in fluid communication with the line;
  a first manifold line in fluid communication with the Y or T-connector;

24 a second manifold line in fluid communication with the Y or T-connector;
a plurality of multi-chamber medical fluid containers each including a first chamber and a second chamber;
a plurality of first filling lines in fluid communication with the first manifold line and the first chambers of the plurality of multi-chamber medical fluid containers;
a plurality of second filling lines in fluid communication with the second manifold line and the second chambers of the plurality of multi-chamber medical fluid containers; and
at least one sterilizing filter located (i) upstream of the Y or T-connector or (ii) in each of the first and second manifold lines.

2. The tubing set of claim 1, wherein the Y or T-connector is a first Y or T-connector, and wherein the tubing set includes a second Y or T-connector located (i) between a leg of the first Y or T-connector and one of first or second manifold lines or (ii) upstream of the at least one sterilizing filter when the at least one sterilizing filter is located upstream of the first Y or T-connector, and wherein a disposable drain line extends from a leg of the second Y or T-connector.

3. The tubing set of claim 1, wherein at least one of the plurality of multi-chamber medical fluid containers includes a third chamber, the third chamber prefilled with a component solution.

4. The tubing set of claim 1, wherein at least one of the plurality of multi-chamber medical fluid containers includes a third chamber, and wherein the tubing set includes a third filling line in fluid communication with the third chamber and in selective fluid communication with the line for connecting to the machine or to a fluid carrying structure extending from the machine.

5. The tubing set of claim 1, wherein the first chamber and the second chamber are separated by a frangible seal which, when broken, allows solutions in the first chamber to mix with solution in the second chamber to form a medical treatment fluid, wherein the medical treatment fluid is a peritoneal dialysis fluid ready to use.

6. The tubing set of claim 1, wherein the plurality of multi-chamber medical fluid containers include a further outlet port for allowing a mixed fluid to be fluidly communicated for treatment.

7. The tubing set of claim 1 further comprising a fluid carrying structure extending from the machine combined to define a tubing assembly, wherein the fluid carrying structure extending from the machine includes a reusable filter, being an ultrafilter or dialyzer, having an inlet line configured to connect to the machine or a line extending from the machine, wherein the tubing set is assembled and sterilized originally in a first package and the ultrafilter or dialyzer and inlet line are assembled and sterilized originally in a second package.

8. The tubing set of claim 7, wherein the inlet line is a reusable supply line and the reusable filter includes an outlet port, an inlet connector of the tubing set being removably connected to the outlet port, an inlet port of the reusable filter being connected to the reusable supply line that is configured for connection to a dialysis fluid outlet port of a dialysis machine, the inlet port and the outlet port of the reusable filter being separated by a semipermeable membrane, the reusable filter also comprising a priming line exiting form the reusable filter.

* * * * *